(12) United States Patent
Edwards et al.

(10) Patent No.: US 8,425,462 B2
(45) Date of Patent: Apr. 23, 2013

(54) DEVICES, SYSTEMS, AND METHODS FOR MEDICAMENT DELIVERY

(75) Inventors: Eric Shawn Edwards, Midlothian, VA (US); Evan Thomas Edwards, Gordonsville, VA (US)

(73) Assignee: Intelliject, Inc., Richmond, VA (US)

( * ) Notice: Subject to any disclaimer, the term of this patent is extended or adjusted under 35 U.S.C. 154(b) by 0 days.

(21) Appl. No.: 13/353,769

(22) Filed: Jan. 19, 2012

(65) Prior Publication Data

US 2012/0123385 A1 May 17, 2012

Related U.S. Application Data

(60) Continuation of application No. 12/794,014, filed on Jun. 4, 2010, now Pat. No. 8,105,281, which is a continuation of application No. 12/138,987, filed on Jun. 13, 2008, now Pat. No. 7,731,690, which is a division of application No. 10/515,571, filed as application No. PCT/US2004/039386 on Nov. 23, 2004, now Pat. No. 7,416,540.

(51) Int. Cl.
*A61M 5/20* (2006.01)

(52) U.S. Cl.
USPC .......................... 604/135; 604/140; 604/141

(58) Field of Classification Search .......... 604/135–137, 604/140, 141, 143–145, 506
See application file for complete search history.

(56) References Cited

U.S. PATENT DOCUMENTS

| | | | |
|---|---|---|---|
| 2,960,087 A | 11/1960 | Uytenbogaart | |
| 3,055,362 A | 9/1962 | Uytenbogaart | |
| 3,115,133 A | 12/1963 | Morando | |
| 3,426,448 A | 2/1969 | Sarnoff | |
| 3,688,765 A | 9/1972 | Gasaway | |
| 3,768,472 A | 10/1973 | Hodosh et al. | |
| 3,795,061 A | 3/1974 | Sarnoff et al. | |
| 3,945,379 A | 3/1976 | Pritz et al. | |
| 4,031,889 A | 6/1977 | Pike | |
| 4,108,177 A | 8/1978 | Pistor | |

(Continued)

FOREIGN PATENT DOCUMENTS

| DE | 2019296 | 11/1971 |
|---|---|---|
| EP | 1712178 A2 | 10/2006 |

(Continued)

OTHER PUBLICATIONS

"Solutions for Medical Devices," 3M Brochure, © 3M 2006 80-6201-3490-0.

(Continued)

*Primary Examiner* — Victoria P Shumate
*Assistant Examiner* — Gerald Landry, II

(57) ABSTRACT

An apparatus includes a housing, a medicament container, an actuator, and a biasing member. The actuator is configured to move the medicament container within the housing when the actuator is moved from a first configuration to a second configuration. The actuator includes a gas container and a puncturer. When the actuator is in the first configuration, a portion of the puncturer is disposed apart from the gas container. When the actuator is in the second configuration, the portion of the puncturer is disposed within the gas container. The gas container has a longitudinal axis offset from a longitudinal axis of the medicament container. The biasing member is configured to bias the actuator toward the second configuration.

17 Claims, 14 Drawing Sheets

U.S. PATENT DOCUMENTS

| | | | |
|---|---|---|---|
| 4,226,235 A | 10/1980 | Sarnoff et al. | |
| 4,258,713 A | 3/1981 | Wardlaw | |
| 4,360,019 A | 11/1982 | Portner et al. | |
| 4,424,057 A | 1/1984 | House | |
| 4,441,629 A | 4/1984 | Mackal | |
| 4,484,910 A | 11/1984 | Sarnoff et al. | |
| 4,573,976 A | 3/1986 | Sampson et al. | |
| 4,596,556 A | 6/1986 | Morrow et al. | |
| 4,610,666 A | 9/1986 | Pizzino | |
| 4,613,328 A | 9/1986 | Boyd | |
| 4,617,557 A | 10/1986 | Gordon | |
| 4,624,660 A | 11/1986 | Mijers et al. | |
| 4,640,686 A | 2/1987 | Dalling et al. | |
| 4,643,721 A | 2/1987 | Brunet | |
| 4,666,430 A | 5/1987 | Brown et al. | |
| 4,673,657 A | 6/1987 | Christian | |
| 4,689,042 A | 8/1987 | Sarnoff et al. | |
| 4,693,708 A | 9/1987 | Wanderer et al. | |
| 4,755,169 A | 7/1988 | Sarnoff et al. | |
| 4,781,697 A | 11/1988 | Slaughter | |
| 4,782,841 A | 11/1988 | Lopez | |
| 4,784,652 A | 11/1988 | Wikström | |
| 4,795,433 A | 1/1989 | Sarnoff | |
| 4,853,521 A | 8/1989 | Claeys et al. | |
| 4,874,382 A | 10/1989 | Lindemann et al. | |
| 4,894,054 A * | 1/1990 | Miskinyar | 604/136 |
| 4,906,235 A | 3/1990 | Roberts | |
| 4,915,695 A | 4/1990 | Koobs | |
| 4,941,880 A | 7/1990 | Burns | |
| 4,959,056 A | 9/1990 | Dombrowski et al. | |
| 4,968,302 A | 11/1990 | Schluter et al. | |
| 4,983,164 A | 1/1991 | Hook et al. | |
| 5,000,736 A | 3/1991 | Kaufhold, Jr. et al. | |
| 5,024,656 A | 6/1991 | Gasaway et al. | |
| 5,037,306 A | 8/1991 | van Schoonhoven | |
| 5,038,023 A | 8/1991 | Saliga | |
| 5,041,088 A | 8/1991 | Ritson et al. | |
| 5,062,603 A | 11/1991 | Smith et al. | |
| 5,064,413 A | 11/1991 | McKinnon et al. | |
| 5,071,353 A | 12/1991 | van der Wal | |
| 5,085,642 A | 2/1992 | Sarnoff et al. | |
| 5,092,843 A | 3/1992 | Monroe et al. | |
| 5,125,898 A | 6/1992 | Kaufhold, Jr. et al. | |
| 5,167,641 A | 12/1992 | Schmitz | |
| 5,199,949 A | 4/1993 | Haber et al. | |
| 5,224,936 A | 7/1993 | Gallagher | |
| 5,240,146 A | 8/1993 | Smedley et al. | |
| 5,281,198 A | 1/1994 | Haber et al. | |
| 5,286,258 A | 2/1994 | Haber et al. | |
| 5,298,023 A | 3/1994 | Haber et al. | |
| 5,312,326 A | 5/1994 | Myers et al. | |
| 5,314,412 A | 5/1994 | Rex | |
| 5,343,519 A | 8/1994 | Feldman | |
| 5,344,407 A | 9/1994 | Ryan | |
| 5,354,284 A | 10/1994 | Haber et al. | |
| 5,356,376 A | 10/1994 | Milijasevic et al. | |
| 5,358,489 A | 10/1994 | Wyrick | |
| 5,363,842 A | 11/1994 | Mishelevich et al. | |
| 5,380,281 A | 1/1995 | Tomellini et al. | |
| 5,383,851 A | 1/1995 | McKinnon, Jr. et al. | |
| 5,399,163 A | 3/1995 | Peterson et al. | |
| 5,417,660 A | 5/1995 | Martin | |
| 5,451,210 A | 9/1995 | Kramer et al. | |
| 5,466,217 A | 11/1995 | Myers et al. | |
| 5,478,316 A | 12/1995 | Bitdinger et al. | |
| 5,514,097 A | 5/1996 | Knauer | |
| 5,514,135 A | 5/1996 | Earle | |
| 5,540,664 A | 7/1996 | Wyrick | |
| 5,558,679 A | 9/1996 | Tuttle | |
| 5,567,160 A | 10/1996 | Massino | |
| 5,568,555 A | 10/1996 | Shamir | |
| 5,569,192 A | 10/1996 | van der Wal | |
| 5,584,815 A | 12/1996 | Pawelka et al. | |
| 5,615,771 A | 4/1997 | Hollister | |
| 5,616,132 A | 4/1997 | Newman | |
| 5,645,534 A | 7/1997 | Chanoch | |
| 5,658,259 A | 8/1997 | Pearson et al. | |
| 5,681,291 A | 10/1997 | Galli | |
| 5,681,292 A | 10/1997 | Tober et al. | |
| 5,695,476 A | 12/1997 | Harris | |
| 5,716,338 A | 2/1998 | Hjertman et al. | |
| 5,772,635 A | 6/1998 | Dastur et al. | |
| 5,792,190 A | 8/1998 | Olson et al. | |
| 5,800,397 A | 9/1998 | Wilson et al. | |
| 5,805,423 A | 9/1998 | Wever et al. | |
| 5,809,997 A | 9/1998 | Wolf | |
| 5,814,020 A | 9/1998 | Gross | |
| 5,832,488 A | 11/1998 | Eberhardt | |
| 5,837,546 A | 11/1998 | Allen et al. | |
| RE35,986 E | 12/1998 | Ritson et al. | |
| 5,846,089 A | 12/1998 | Weiss et al. | |
| 5,852,590 A | 12/1998 | de la Huerga | |
| 5,853,292 A | 12/1998 | Eggert et al. | |
| 5,858,001 A * | 1/1999 | Tsals et al. | 604/135 |
| 5,868,713 A | 2/1999 | Klippenstein | |
| 5,868,721 A | 2/1999 | Marinacci et al. | |
| D407,487 S | 3/1999 | Greubel et al. | |
| 5,925,021 A | 7/1999 | Castellano et al. | |
| 5,928,195 A | 7/1999 | Malamud et al. | |
| 5,941,857 A | 8/1999 | Nguyen et al. | |
| 5,964,739 A | 10/1999 | Champ | |
| 5,971,953 A | 10/1999 | Bachynsky | |
| 6,015,438 A | 1/2000 | Shaw | |
| 6,039,713 A | 3/2000 | Botich et al. | |
| 6,045,534 A | 4/2000 | Jacobsen et al. | |
| 6,050,977 A | 4/2000 | Adams | |
| 6,056,728 A | 5/2000 | Von Schuckmann | |
| 6,062,901 A | 5/2000 | Liu et al. | |
| 6,063,053 A | 5/2000 | Castellano et al. | |
| 6,074,213 A | 6/2000 | Hon | |
| 6,077,106 A | 6/2000 | Mish | |
| 6,083,199 A | 7/2000 | Thorley et al. | |
| 6,084,526 A | 7/2000 | Blotky et al. | |
| 6,086,562 A | 7/2000 | Jacobsen et al. | |
| 6,096,002 A | 8/2000 | Landau | |
| 6,099,504 A | 8/2000 | Gross et al. | |
| 6,102,896 A | 8/2000 | Roser | |
| 6,119,684 A | 9/2000 | Nöhl et al. | |
| 6,149,626 A | 11/2000 | Rachynsky et al. | |
| 6,158,613 A | 12/2000 | Novosel et al. | |
| 6,161,281 A | 12/2000 | Dando et al. | |
| 6,165,155 A | 12/2000 | Jacobsen et al. | |
| 6,179,812 B1 | 1/2001 | Botich et al. | |
| 6,193,695 B1 | 2/2001 | Rippstein, Jr. | |
| 6,202,642 B1 | 3/2001 | McKinnon et al. | |
| 6,210,359 B1 | 4/2001 | Patel et al. | |
| 6,210,369 B1 | 4/2001 | Wilmot et al. | |
| 6,219,587 B1 | 4/2001 | Ahlin et al. | |
| 6,221,045 B1 | 4/2001 | Duchon et al. | |
| 6,221,055 B1 | 4/2001 | Shaw et al. | |
| 6,245,046 B1 | 6/2001 | Sibbitt | |
| 6,258,063 B1 | 7/2001 | Haar et al. | |
| 6,258,068 B1 | 7/2001 | Kirchhofer et al. | |
| 6,259,654 B1 | 7/2001 | de la Huerga | |
| 6,264,629 B1 | 7/2001 | Landau | |
| 6,270,479 B1 | 8/2001 | Bergens et al. | |
| 6,280,421 B1 | 8/2001 | Kirchhofer et al. | |
| 6,312,412 B1 | 11/2001 | Saied et al. | |
| 6,317,630 B1 | 11/2001 | Gross et al. | |
| 6,334,070 B1 | 12/2001 | Nova et al. | |
| 6,364,866 B1 | 4/2002 | Furr et al. | |
| 6,371,939 B2 | 4/2002 | Bergens et al. | |
| 6,387,078 B1 | 5/2002 | Gillespie, III | |
| 6,405,912 B2 | 6/2002 | Giannou | |
| 6,406,455 B1 | 6/2002 | Willis et al. | |
| 6,411,567 B1 | 6/2002 | Niemiec et al. | |
| 6,413,236 B1 | 7/2002 | Van Dyke | |
| 6,425,897 B2 | 7/2002 | Overes et al. | |
| 6,428,517 B1 | 8/2002 | Hochman et al. | |
| 6,428,528 B2 | 8/2002 | Sadowski et al. | |
| 6,475,181 B1 | 11/2002 | Potter et al. | |
| 6,478,771 B1 | 11/2002 | Lavi et al. | |
| 6,494,863 B1 | 12/2002 | Shaw et al. | |
| 6,500,150 B1 | 12/2002 | Gross et al. | |
| 6,514,230 B1 | 2/2003 | Munk et al. | |
| 6,529,446 B1 | 3/2003 | de la Huerga | |
| 6,530,900 B1 | 3/2003 | Dailey et al. | |

| Patent No. | Date | Inventor(s) | | Patent No. | Date | Inventor(s) |
|---|---|---|---|---|---|---|
| 6,530,904 B1 | 3/2003 | Edwards et al. | | 7,416,540 B2 | 8/2008 | Edwards et al. |
| 6,535,714 B1 | 3/2003 | Melker et al. | | 7,465,294 B1 | 12/2008 | Vladimirsky |
| 6,540,675 B2 | 4/2003 | Aceti et al. | | 7,500,963 B2 | 3/2009 | Westbye et al. |
| 6,544,234 B1 | 4/2003 | Gabriel | | 7,500,967 B2 | 3/2009 | Thorley et al. |
| 6,551,276 B1 | 4/2003 | Mann et al. | | 7,554,188 B2 | 6/2009 | Hauenstein |
| 6,551,298 B1 | 4/2003 | Zhang | | 7,637,891 B2 * | 12/2009 | Wall ............ 604/131 |
| 6,554,798 B1 | 4/2003 | Mann et al. | | 7,648,482 B2 | 1/2010 | Edwards et al. |
| 6,558,320 B1 | 5/2003 | Causey, III et al. | | 7,648,483 B2 | 1/2010 | Edwards et al. |
| 6,569,123 B2 | 5/2003 | Alchas et al. | | 7,674,246 B2 | 3/2010 | Gillespie et al. |
| 6,572,584 B1 | 6/2003 | Shaw et al. | | 7,731,686 B2 | 6/2010 | Edwards et al. |
| 6,574,166 B2 | 6/2003 | Niemiec | | 7,731,690 B2 | 6/2010 | Edwards et al. |
| 6,575,939 B1 | 6/2003 | Brunel | | 7,749,194 B2 | 7/2010 | Edwards et al. |
| RE38,189 E | 7/2003 | Walker et al. | | 7,918,823 B2 | 4/2011 | Edwards et al. |
| 6,585,685 B2 | 7/2003 | Staylor et al. | | 7,947,017 B2 | 5/2011 | Edwards et al. |
| 6,585,698 B1 | 7/2003 | Packman et al. | | 8,016,788 B2 | 9/2011 | Edwards et al. |
| 6,589,158 B2 | 7/2003 | Winkler | | 8,105,281 B2 | 1/2012 | Edwards et al. |
| 6,595,956 B1 | 7/2003 | Gross et al. | | 8,123,719 B2 | 2/2012 | Edwards et al. |
| 6,597,794 B2 | 7/2003 | Cole et al. | | 8,172,082 B2 | 5/2012 | Edwards et al. |
| 6,599,272 B1 | 7/2003 | Hjertman et al. | | 2001/0005781 A1 | 6/2001 | Bergens et al. |
| 6,616,627 B2 | 9/2003 | Willis et al. | | 2001/0037087 A1 | 11/2001 | Knauer |
| 6,633,796 B1 | 10/2003 | Pool et al. | | 2002/0074345 A1 | 6/2002 | Schneider et al. |
| 6,641,566 B2 | 11/2003 | Douglas et al. | | 2002/0076679 A1 | 6/2002 | Aman |
| 6,645,181 B1 | 11/2003 | Lavi et al. | | 2003/0028145 A1 | 2/2003 | Duchon et al. |
| 6,648,850 B2 | 11/2003 | Landau | | 2003/0040717 A1 | 2/2003 | Saulenas et al. |
| 6,673,035 B1 | 1/2004 | Rice et al. | | 2003/0105430 A1 | 6/2003 | Lavi et al. |
| 6,676,630 B2 | 1/2004 | Landau et al. | | 2003/0106824 A1 | 6/2003 | Wilmot et al. |
| 6,689,093 B2 | 2/2004 | Landau | | 2003/0132128 A1 | 7/2003 | Mazur |
| 6,692,469 B1 | 2/2004 | Weekes et al. | | 2003/0135388 A1 | 7/2003 | Martucci et al. |
| 6,702,778 B2 | 3/2004 | Hill et al. | | 2003/0171717 A1 * | 9/2003 | Farrugia et al. ............ 604/131 |
| 6,706,019 B1 | 3/2004 | Parker et al. | | 2003/0233070 A1 | 12/2003 | De La Serna et al. |
| 6,707,763 B2 | 3/2004 | Osberg et al. | | 2004/0015125 A1 | 1/2004 | Alexandre et al. |
| 6,708,050 B2 | 3/2004 | Carim | | 2004/0019326 A1 | 1/2004 | Gilbert et al. |
| 6,722,916 B2 | 4/2004 | Buccinna et al. | | 2004/0024361 A1 | 2/2004 | Fago et al. |
| 6,723,077 B2 | 4/2004 | Pickup et al. | | 2004/0039336 A1 | 2/2004 | Amark et al. |
| 6,726,657 B1 | 4/2004 | Dedig et al. | | 2004/0039337 A1 | 2/2004 | Letzing |
| 6,726,661 B2 | 4/2004 | Munk et al. | | 2004/0039368 A1 | 2/2004 | Reilly et al. |
| 6,736,796 B2 | 5/2004 | Shekalim | | 2004/0054327 A1 | 3/2004 | Gillespie, III |
| 6,743,635 B2 | 6/2004 | Neel et al. | | 2004/0073169 A1 | 4/2004 | Amisar et al. |
| 6,749,437 B2 | 6/2004 | Chan | | 2004/0092874 A1 | 5/2004 | Mazidji |
| 6,752,781 B2 | 6/2004 | Landau et al. | | 2004/0094146 A1 | 5/2004 | Schiewe et al. |
| 6,767,336 B1 | 7/2004 | Kaplan | | 2004/0116854 A1 | 6/2004 | Abulhaj et al. |
| 6,770,052 B2 | 8/2004 | Hill et al. | | 2004/0138611 A1 | 7/2004 | Griffiths et al. |
| 6,783,509 B1 | 8/2004 | Landau et al. | | 2004/0143298 A1 | 7/2004 | Nova et al. |
| 6,786,875 B2 | 9/2004 | Barker et al. | | 2004/0159364 A1 | 8/2004 | Landau et al. |
| 6,793,646 B1 | 9/2004 | Giambattista et al. | | 2004/0220524 A1 | 11/2004 | Sadowski et al. |
| 6,803,856 B1 | 10/2004 | Murphy et al. | | 2004/0249358 A1 | 12/2004 | McWethy et al. |
| 6,808,514 B2 | 10/2004 | Schneider et al. | | 2004/0267204 A1 | 12/2004 | Brustowicz |
| 6,809,653 B1 | 10/2004 | Mann et al. | | 2005/0033234 A1 | 2/2005 | Sadowski et al. |
| 6,817,986 B2 | 11/2004 | Slate et al. | | 2005/0033386 A1 | 2/2005 | Osborn et al. |
| 6,830,560 B1 | 12/2004 | Gross et al. | | 2005/0062603 A1 | 3/2005 | Fuerst et al. |
| 6,839,304 B2 | 1/2005 | Niemiec et al. | | 2005/0090781 A1 | 4/2005 | Baba et al. |
| 6,872,200 B2 | 3/2005 | Mann et al. | | 2005/0101912 A1 | 5/2005 | Faust et al. |
| 6,875,195 B2 | 4/2005 | Choi | | 2005/0134433 A1 | 6/2005 | Sweeney et al. |
| 6,883,222 B2 | 4/2005 | Landau | | 2005/0148931 A1 | 7/2005 | Juhasz |
| 6,923,764 B2 | 8/2005 | Aceti et al. | | 2005/0148945 A1 | 7/2005 | Chen |
| 6,936,029 B2 | 8/2005 | Mann et al. | | 2005/0159705 A1 | 7/2005 | Crawford et al. |
| 6,937,150 B2 | 8/2005 | Medema et al. | | 2005/0165360 A1 | 7/2005 | Stamp |
| 6,942,646 B2 | 9/2005 | Langley et al. | | 2005/0171477 A1 | 8/2005 | Rubin et al. |
| 6,946,299 B2 | 9/2005 | Neel et al. | | 2005/0182358 A1 | 8/2005 | Veit et al. |
| 6,949,082 B2 | 9/2005 | Langley et al. | | 2005/0197654 A1 | 9/2005 | Edman et al. |
| 6,952,604 B2 | 10/2005 | DeNuzzio et al. | | 2005/0222539 A1 | 10/2005 | Gonzales et al. |
| 6,953,445 B2 | 10/2005 | Wilmot et al. | | 2005/0261742 A1 | 11/2005 | Nova et al. |
| 6,953,693 B2 | 10/2005 | Neel et al. | | 2005/0267403 A1 | 12/2005 | Landau et al. |
| 6,958,691 B1 | 10/2005 | Anderson et al. | | 2005/0277891 A1 | 12/2005 | Sibbitt |
| 6,959,247 B2 | 10/2005 | Neel et al. | | 2006/0030819 A1 | 2/2006 | Young et al. |
| 6,961,285 B2 | 11/2005 | Niemiec et al. | | 2006/0053036 A1 | 3/2006 | Coffman et al. |
| 6,964,650 B2 | 11/2005 | Alexandre et al. | | 2006/0058848 A1 | 3/2006 | Piraino et al. |
| 6,969,259 B2 | 11/2005 | Pastrick et al. | | 2006/0111666 A1 | 5/2006 | Hommann et al. |
| 6,979,316 B1 * | 12/2005 | Rubin et al. ............ 604/156 | | 2006/0111671 A1 | 5/2006 | Klippenstein |
| 6,979,326 B2 | 12/2005 | Mann et al. | | 2006/0129090 A1 | 6/2006 | Moberg et al. |
| 6,985,870 B2 | 1/2006 | Martucci et al. | | 2006/0189938 A1 | 8/2006 | Hommann et al. |
| 6,997,911 B2 | 2/2006 | Klitmose | | 2006/0200077 A1 | 9/2006 | Righi et al. |
| 7,014,470 B2 | 3/2006 | Vann | | 2006/0235354 A1 | 10/2006 | Kaal et al. |
| 7,074,211 B1 | 7/2006 | Heiniger et al. | | 2006/0247579 A1 | 11/2006 | Friedman |
| 7,113,101 B2 | 9/2006 | Petersen et al. | | 2006/0265186 A1 | 11/2006 | Holland et al. |
| 7,116,233 B2 | 10/2006 | Zhurin | | 2007/0008113 A1 | 1/2007 | Spoonhower et al. |
| 7,126,879 B2 | 10/2006 | Snyder | | 2007/0074722 A1 | 4/2007 | Giroux et al. |
| 7,158,011 B2 | 1/2007 | Brue | | 2007/0129686 A1 | 6/2007 | Daily et al. |
| 7,357,790 B2 | 4/2008 | Hommann et al. | | 2007/0135767 A1 | 6/2007 | Gillespie, III et al. |

| | | |
|---|---|---|
| 2007/0184847 A1 | 8/2007 | Hansen et al. |
| 2007/0210147 A1 | 9/2007 | Morrone et al. |
| 2007/0213598 A1 | 9/2007 | Howard et al. |
| 2008/0059133 A1 | 3/2008 | Edwards et al. |
| 2008/0154200 A1 | 6/2008 | Lesch |
| 2008/0188798 A1 | 8/2008 | Weber |
| 2008/0255513 A1 | 10/2008 | Kaal et al. |
| 2009/0093759 A1 | 4/2009 | Judd et al. |
| 2009/0192486 A1 | 7/2009 | Wilmot et al. |
| 2009/0221962 A1 | 9/2009 | Kaal et al. |
| 2009/0318361 A1 | 12/2009 | Noera et al. |
| 2010/0049125 A1 | 2/2010 | James et al. |
| 2010/0152659 A1 | 6/2010 | Streit et al. |
| 2010/0160894 A1 | 6/2010 | Julian et al. |
| 2010/0185148 A1 | 7/2010 | Gillespie, III et al. |
| 2011/0196300 A1 | 8/2011 | Edwards et al. |
| 2011/0319822 A1 | 12/2011 | Edwards et al. |
| 2012/0071829 A1 | 3/2012 | Edwards et al. |
| 2012/0116318 A1 | 5/2012 | Edwards et al. |

FOREIGN PATENT DOCUMENTS

| | | |
|---|---|---|
| FR | 1514 210 | 2/1968 |
| FR | 2 509 615 | 1/1983 |
| FR | 2 700 959 | 2/1993 |
| WO | WO 91/04760 A1 | 4/1991 |
| WO | WO 95/26009 | 9/1995 |
| WO | WO 95/35126 | 12/1995 |
| WO | WO 01/24690 A2 | 4/2001 |
| WO | WO 01/26020 A1 | 4/2001 |
| WO | WO 01/88828 | 11/2001 |
| WO | WO 01/93926 A2 | 12/2001 |
| WO | WO 02/083205 A1 | 10/2002 |
| WO | WO 02/083212 A1 | 10/2002 |
| WO | WO 03/011378 A1 | 2/2003 |
| WO | WO 03/013632 A2 | 2/2003 |
| WO | WO 03/095001 A1 | 11/2003 |
| WO | WO 03/097133 A1 | 11/2003 |
| WO | WO 2004/047890 A1 | 6/2004 |
| WO | WO 2004/047891 A1 | 6/2004 |
| WO | WO 2004/047892 A1 | 6/2004 |
| WO | WO 2004/047893 A1 | 6/2004 |
| WO | WO 2004/054644 | 7/2004 |
| WO | WO 2005/050526 A2 | 6/2005 |
| WO | WO 2005/070481 A1 | 8/2005 |
| WO | WO 2005/077441 A2 | 8/2005 |
| WO | WO 2006/109778 A1 | 10/2006 |

OTHER PUBLICATIONS

Merle Tingelstad, "Revolutionary Medical Technology Increases Demand for Flexible Interconnects," [online] May 15, 2006 [retrieved on Nov. 15, 2006] Retrieved from the Internet <URL: http://www.ecnmag.com/index.asp?layout=articlePrint &ArticleID=CA6332947 >.

"Flexible circuits / Flex circuits / Flexible Technology Ltd.," Flexible Technology Limited [online] [retrieved on Aug. 28, 2006] Retrieved from the Internet <URL: http://www.flexibletechnology.com/>.

"Flexible circuits capabilities of Flexible Technology Limited," Our Flexible Circuits Capabilities [online] [retrieved on Aug. 28, 2006] Retrieved from the Internet <URL: http://www.flexibletechnology.com/Flexible circuits Capability.htm >.

"Flex Circuits/flexible circuits design guide," [online] [retrieved on Aug. 28, 2006] Retrieved from the Internet <URL: http://flexiblecircuit.co.uk/Flex Circuits Design Guide.htm >.

"Insect Stings Auto-injector Pouches and Carry Cases," The Insect Stings On-Line Shop, [online] [retrieved on Jan. 24, 2007] Retrieved from the Internet <URL: http://www.insectstings.co.uk/acatalog/Auto Injector Pouches.html >.

"Anaphylaxis Canada Product Catalogue," Anaphylaxis Canada > Living with Anaphylaxis > Tools and Resources [online] [retrieved on Jan. 24, 2007] Retrieved from the Internet <URL: http://anaphylaxis.org/content/livingwith/productcatalogue.asp >.

"Microfluidics Device Provides Programmed, Long-Term Drug Dosing," nano techwire.com [online] [retrieved on Nov. 28, 2006] Retrieved from the Internet <URL: http://nanotechwire.com/news.asp?nid=3141&ntid=124&pg=1 >.

Roger Allan, "Medical Electronics: Technology Advances Will Revolutionize Healthcare," Sep. 30, 2002 [online] [retrieved on Nov. 28, 2006] Retrieved from the Internet <URL: http://www.elecdesign.com/Articles/Index.cfm?AD=1&ArticleID=2041>.

RFID Gazette, "Smart Labels in Healthcare," Sep. 29, 2005 [online] [retrieved on Nov. 28, 2006] Retrieved from the Internet <URL: http://www.rfidagazeete.org/2005/09/smart labels in.html >.

"Merck Serono Launches easypod(R), First Electronic Growth Hormone Injection Device," Jan. 30, 2007 [online] [retrieved on Feb. 5, 2007] Retrieved from the Internet <URL: http://www.biz.yahoo.com/prnews/070130/ukm028.html?.v=8.

Dr. Oliver Scholz, "Drug depot in a tooth," [online] [retrieved on Feb. 6, 2007] Retrieved from the Internet <URL: http://www.fraunhofer.de/fhg/EN/press/pi/2007/02Mediendienst22007Thema2jsp?print=true.

Heartsine Technology, samaritan™ Pad Accessories [online] [retrieved on Jun. 1, 2007] Retrieved from the Internet <URL: http://www.heartsine.com/aboutsam-accessories.htm>.

CliniSense Corporation, "Drug delivery devices a potentially harsh environment for drugs," Stability [online] [retrieved on Jun. 1, 2007] Retrieved from the Internet <URL: http://www.clinisense.com/devices.htm>.

CliniSense Corporation, "LifeTrack Technology a new method to detect improper storage." Stability [online] [retrieved on Jun. 1, 2007] Retrieved from the Internet <URL: http://www.clinisense.com/tech.htm>.

AED Professionals™ Brochure [online] [retrieved on Jun. 1, 2007] Retrieved from the Internet <URL: http://www.aedprofessionals.com/>.

Daniel Ruppar, "Implant Technologies Expected to Remain a Niche but Effective Method of Drug Delivery," Drug Delivery Technology, Feb. 2007, vol. 7, No. 2 [online] [retrieved on Jun. 1, 2007] Retrieved from the Internet <URL: http://www.drugdeliverytech-online.com/drugdelivery/200702/templates/pageviewer_print?pg=44&pm=8 >.

Search Report and Written Opinion for International Patent Application No. PCT/US06/03415 mailed Jul. 13, 2006, 10 pages.

Search Report and Written Opinion for International Patent Application No. PCT/US07/84891 mailed Sep. 15, 2008, 7 pages.

Search Report and Written Opinion for International Patent Application No. PCT/US07/007626 mailed Sep. 29, 2008.

Examination Report for British Patent Application No. GB 0708523.6, mailed Dec. 8, 2008.

Examination Report for British Patent Application No. GB 0822532.8, mailed Jan. 21, 2009.

Office Action for U.S. Appl. No. 11/562,061, mailed Feb. 3, 2009.

Examination Report for British Patent Application No. GB 0822532.8, mailed May 21, 2009.

Office Action for U.S. Appl. No. 12/138,987, mailed Oct. 5, 2009.

Office Action for U.S. Appl. No. 11/758,393, mailed May 13, 2009.

Office Action for U.S. Appl. No. 11/566,422, mailed Jul. 6, 2010.

Office Action for U.S. Appl. No. 13/090,392, mailed Feb. 29, 2012.

Office Action for U.S. Appl. No. 11/566,422, mailed Dec. 3, 2010.

Office Action for Japanese Patent Application No. 2009-537380, mailed Jun. 15, 2012.

Office Action for Canadian Patent Application No. CA 2,586,525, mailed Aug. 17, 2010.

\* cited by examiner

DEVICES, SYSTEMS, AND METHODS FOR MEDICAMENT DELIVERY

CROSS-REFERENCE TO RELATED APPLICATIONS

This application is a continuation of U.S. patent application Ser. No. 12/794,014, entitled "Devices, Systems and Methods for Medicament Delivery," filed Jun. 4, 2010, which is a continuation of U.S. patent application Ser. No. 12/138, 987, now U.S. Pat. No. 7,731,690, entitled "Devices, Systems and Methods for Medicament Delivery," filed Jun. 13, 2008, which is a divisional of U.S. patent application Ser. No. 10/515,571, now U.S. Pat. No. 7,416,540, entitled "Devices, Systems and Methods for Medicament Delivery," filed Nov. 23, 2004, which is a national stage filing under 35 U.S.C. §371 of International Patent Application No. PCT/US2004/039386, entitled "Devices, Systems and Methods for Medicament Delivery," filed Nov. 23, 2004, each of which is incorporated herein by reference in its entirety.

BACKGROUND

Exposure, such as via ingestion, inhalation, and/or injection, to certain allergens, toxins, and/or other substances can cause profound reactions for some and/or all people and/or animals. For example, certain people are highly allergic to certain substances, such as peanuts, shellfish, particular drugs, certain proteins, bee venom, insect bites, etc. The allergic response to the exposure can lead to anaphylactic shock, which can cause a sharp drop in blood pressure, hives, and/or substantial breathing difficulties caused by severe airway constriction. As another example, inhalation of certain nerve agents can cause severe physiological trauma. Responding rapidly to such exposures can prevent injury and/or death. For example, in response to an exposure leading to anaphylactic shock, an injection of epinephrine (i.e., adrenaline) can provide substantial and/or complete relief from the reaction. As another example, injection of an antidote to a nerve agent can greatly reduce and/or eliminate the potential harm of the exposure. As yet another example, rapid injection of certain drugs, such as a beta blocker, blood thinner, nitroglycerine, antihistamines, insulin, and opioids, etc., can provide substantial relief from various dangerous medical conditions.

Thus, certain exemplary embodiments provide systems, devices, and/or methods for rapidly injecting a medicament.

SUMMARY

Certain exemplary embodiments comprise an apparatus, comprising: a compressed gas container; a plurality of vials adapted to store a liquid medicament, each vial defining a longitudinal axis, the longitudinal axes of the plurality of vials parallel and non-coaxial, the plurality of vials fluidly coupleable to an actuating portion of a contents of the gas container; and a plurality of pistons, each piston adapted to move within a corresponding vial from the plurality of vials, the plurality of pistons adapted to, in response to discharge of the actuating portion of the contents of the compressed gas container, transfer at least a portion of the liquid medicament from the plurality of vials and through a needle that is extendable into a patient. Certain exemplary embodiments comprise a method comprising a plurality of activities, comprising: discharging an actuating portion of a contents of a compressed gas container, the compressed gas container contained within an apparatus; in reaction to said discharging activity, moving a piston within a vial, the vial one of a plurality of vials contained within the apparatus, each vial adapted to store a liquid medicament, each vial defining a longitudinal axis, the longitudinal axes of the plurality of vials parallel and non-co-axial, the plurality of vials fluidly coupleable to a contents of the gas container; and transferring a liquid medicament from the vial and through a needle that is extendable into a patient.

BRIEF DESCRIPTION OF THE DRAWINGS

A wide variety of potential embodiments will be more readily understood through the following detailed description of certain exemplary embodiments, with reference to the accompanying exemplary drawings in which.

DETAILED DESCRIPTION

Figure 1:
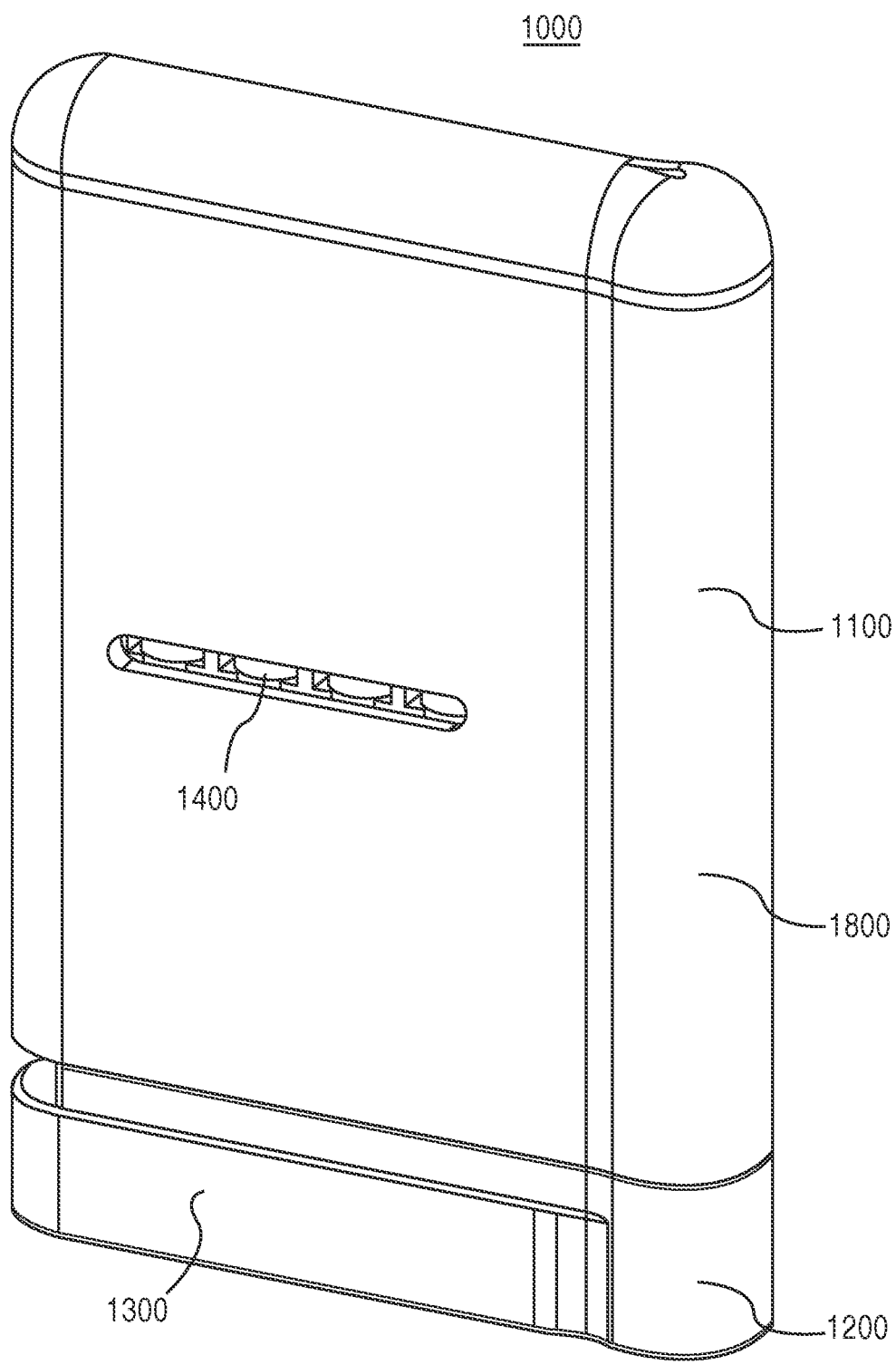
FIG. 1 is a perspective view of an exemplary embodiment of a system 1000.

When the following terms are used herein, the accompanying definitions apply:

actuating portion—that part that puts something into action.

actuation lock—a device adapted to prevent actuation, such as, for example a pivotable, translatable, keyed, squeezable, and/or removable lock.

actuator—a mechanism that puts something into action.

adapted to—suitable or fit for a particular purpose.

apparatus—a mechanism and/or device.

arm—an elongated structural member, which need not be solely linear.

can—is capable of, in at least some embodiments.

channel—a conduit for one or more fluids.

compressed gas—a substantially pressurized substance, such as helium, nitrogen, and/or carbon dioxide, etc., in a gaseous form.

comprising—including but not limited to.

contain—to hold within.

contents—a contained compressed gas.

credit card—a card (usually plastic) that assures a seller that the person using it has a satisfactory credit rating and that the issuer will see to it that the seller receives payment for the merchandise and/or services delivered. Typically measuring in size from approximately 3 to approximately 4 inches in length, such as approximately 3.40 inches, 3.375 inches, 85 millimeters, etc., and from approximately 1.75 to approximately 2.75 inches in width, such as approximately 2.10 inches, 2.2125 inches, 2.5 inches, 55 millimeters, etc.

discharge—to release from confinement; to emit.

eject—to expel.

escape port—an opening for the exit of a gas.

expulsion pressure—a force applied over an area of a liquid, the force sufficient to expel the liquid in a predetermined manner.

extend—to move out and/or away from.

extendable—able to move out and/or away from.

fluid—a gas and/or liquid.

fluidly coupleable—able to be related via a fluid.

frangible—a device that is capable of being broken and/or penetrated to allow fluid to flow therethrough.

housing—something that covers, protects, holds, and/or supports.

in reaction to—responding indirectly and/or directly to.

indicate—to show, mark, signify, denote, evidence, evince, manifest, declare, enunciate, specify, explain, exhibit, present, reveal, disclose, and/or display.

indicator—a device and/or substance that indicates.

liquid medicament—a medicine, medication, drug, pharmaceutical, prescriptive, antidote, anti-venom, hormone, stimulant, vasodilator, anesthetic, and/or nutritional supplement in a substantially liquid form.

may—is allowed to, in at least some embodiments.

needle—a hollow, slender, sharp-pointed instrument used for injection. Includes cannulas.

non-co-axial—not having co-linear axes.

patient—a receiver of a liquid medicament, such as a human, mammal, animal, etc.

piston—a sliding piece which either is moved by, or moves against, fluid pressure.

pivotable—capable of pivoting.

plurality—the state of being plural and/or more than one.

predetermined—established in advance.

puncturer—a device adapted to penetrate using a substantially sharp and/or tapered point, tip, edge, or the like.

pusher—a device adapted to convert fluid pressure to mechanical movement.

retract—to pull inward.

reservoir—a receptacle or chamber for storing and/or directing movement of a fluid.

spring—an elastic device, such as a coil of wire, that regains its original shape after being compressed or extended.

status—a state or condition.

substantially—to a great extent or degree.

system—a collection of mechanisms, devices, data, and/or instructions, the collection designed to perform one or more specific functions.

tip—a terminal end.

transfer—to convey from one place to another.

translatable—capable of being transferred from one place to another and/or of being moved with respect to something else.

valve—a device that regulates flow through a pipe and/or through an aperture by opening, closing, and/or obstructing a port and/or passageway.

vent—to release from confinement.

vial—a closable vessel.

Figure 2:
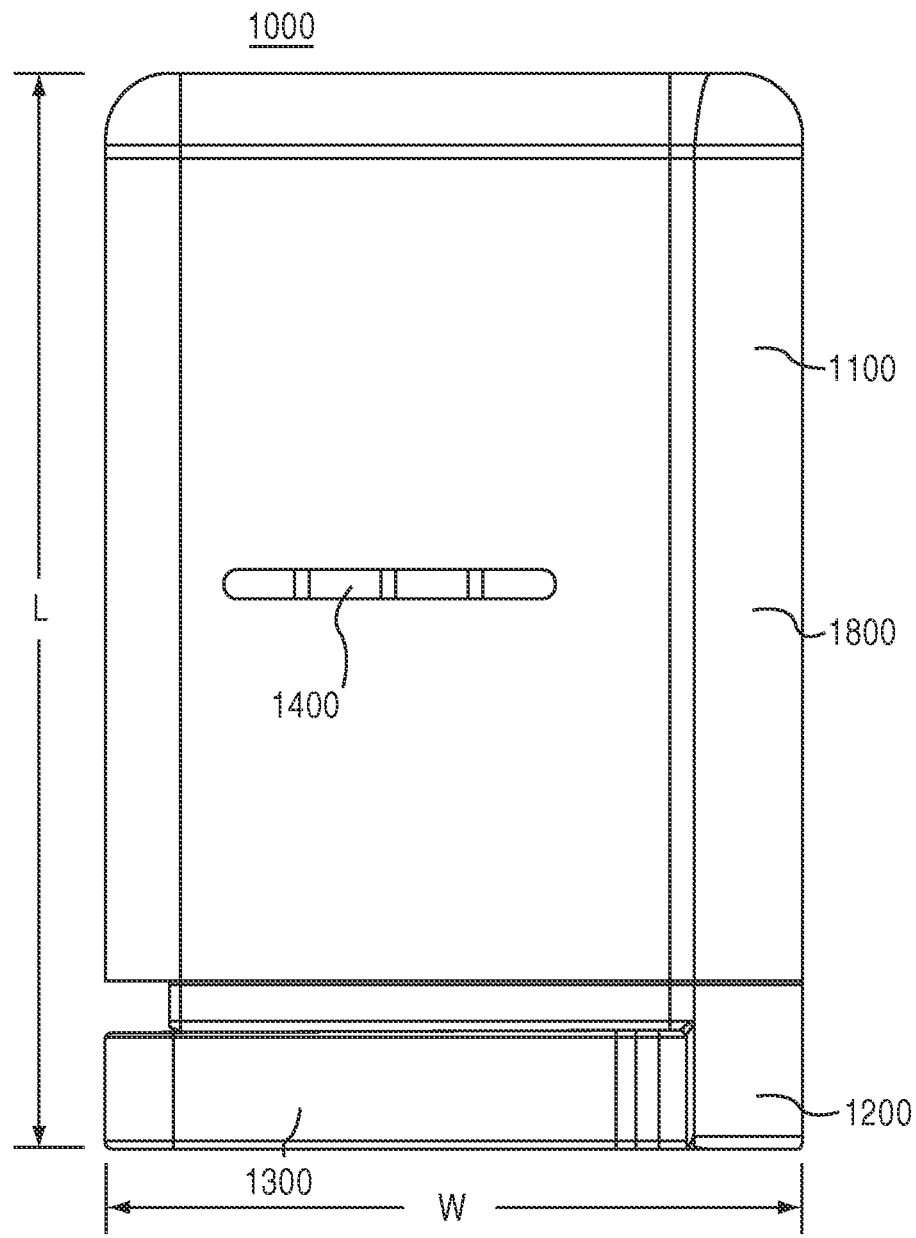
FIG. 2 is a front view of an exemplary embodiment of a system 1000.
Figure 3:
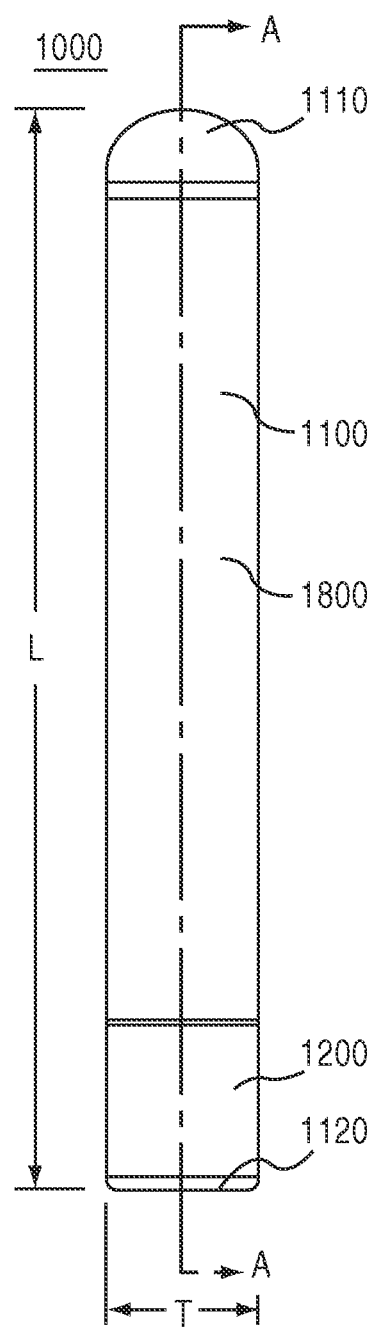
FIG. 3 is a side view of an exemplary embodiment of a system 1000.

FIG. 1 is a perspective view, FIG. 2 is a front view, and FIG. 3 is a side view, of an exemplary embodiment of a system 1000, which can comprise a housing 1100, which, in certain operative embodiments, can comprise a handheld portion 1800 separated via an actuation guard 1200 from an actuation bar 1300. Actuation guard 1200 can prevent accident activation of system 1000. Housing 1100 can be constructed of a durable material, such as stainless steel, aluminum, polycarbonate, etc., to protect a compressed gas container, medicament, injection apparatus and/or user of system 1000. The injection apparatus can be actuated by a fluid pressure, such as pressure provided by the compressed gas, which upon completion of its actuation duties can escape housing 1100 via gas escape opening, such as via status indicator 1400.

A status of a system 1000 can be determined via status indicator 1400, which can provide a view, such as via a UV blocking, photo-sensitive, and/or translucent window, into an interior of housing 1100. Viewable through the window can be a status of medicament carried by housing 1100, a location of a needle and/or injection apparatus for the medicament, and/or an activation status of system 1000. For example, if the medicament has aged to the point of discoloration, which aging might or might not render the medication useless, harmful, etc., status indicator 1400 can allow that situation to be determined. In certain exemplary embodiments, gas can escape housing 1100 via status indicator 1400 and/or another opening in housing 1100.

Certain exemplary embodiments of system 1000 can provide a compact medicament delivery mechanism that can efficiently and/or rapidly deliver a prescribed dose. The length (L) and width (W) of system 1000 can be similar to that of a credit card, and the thickness (T) can be less than one inch. Thus, certain exemplary embodiments of system 1000 can provide a conveniently carried, easy-to-use, easy to activate drug delivery apparatus that can require little to no training to safely carry, use, and/or dispose of.

To assist a user in positioning system 1000 in a correct orientation for injection, system 1000 and/or housing 1100 can provide various tactile clues. For example, a top 1110 of housing 1100 can be rounded, and a bottom 1120 of actuation bar 1300 of housing 1100 can be flat. Other tactile clues are also possible, such as bulges, ribs, grooves, gaps, roughened surfaces, indentations, etc.

Figure 4:
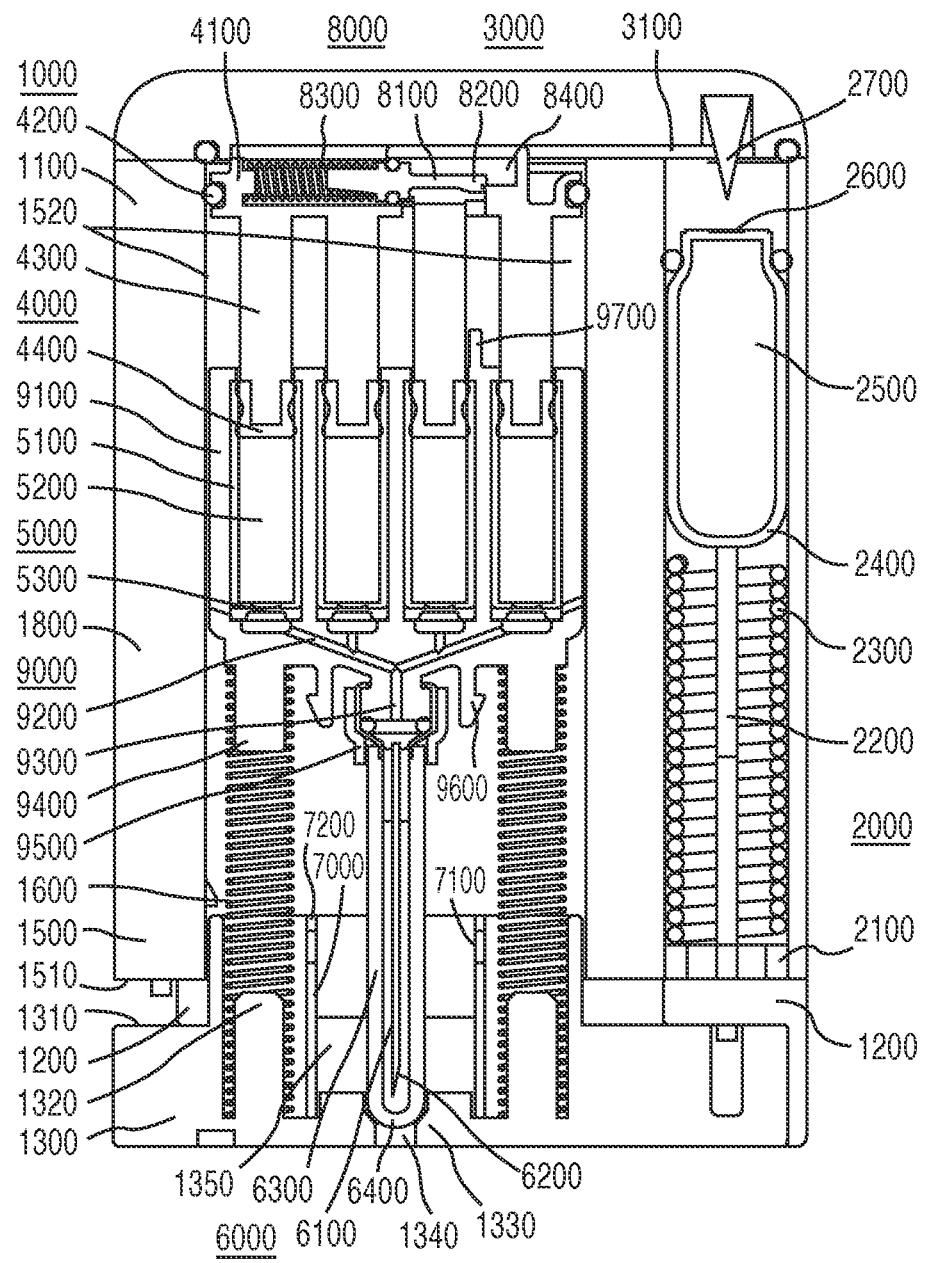
FIG. 4 is a cross-sectional view taken along lines A-A of FIG. 3 of an exemplary embodiment of a system 1000 in a first operative position.

FIG. 4 is a cross-sectional view taken along lines A-A of FIG. 3 of an exemplary embodiment of a system 1000 in a first operative position. FIGS. 5, 6, 7, 8, and 9 show system 1000 of FIG. 4 in second, third, fourth, fifth, and sixth operative positions, respectively.

System 1000 can comprise a housing 1100, handheld portion 1800, actuation guard 1200, and/or actuation bar 1300. System 1000 can comprise system actuator 2000, gas reservoirs 3000, medicament actuator 4000, medicament storage assembly 5000, medicament carrier 9000, needle assembly 6000, use indicator 7000, and/or gas vent mechanism 8000, etc.

Upon removal, release, rotation, and/or relocation of actuation guard 1200, system actuator 2000 can be adapted to rapidly discharge an actuating portion of a contents of a compress gas container. For example, system actuator 2000 can comprise a compressed gas container 2400, which initially can contain a compressed gas 2500, an actuating portion of which can be released from container 2400 by penetration of a gas port 2600 via a point of a puncturer 2700. Upon removal and/or relocation of actuation guard 1200, actuation bar 1300 can be moved closer to and/or in contact with handheld portion 1800. Upon removal and/or relocation of actuation guard 1200, gas container 2400 can be brought into contact with puncturer 2700 via extension of a pre-compressed spring 2300 and/or movement of a actuation stick 2200. Thus, actuation guard 1200 can prevent accident activation of system 1000 and/or unintended discharge of an actuating portion of the contents 2500 of gas container 2400.

Once gas port 2600 has been punctured, an actuating portion of compressed gas 2500 can escape from container 2400 and flow via gas reservoirs 3000, such as gas channel 3100. The flowing gas can meet and/or apply gas pressure to medicament actuator 4000, which can comprise a pusher 4100, which can travel within a sleeve 1500 defined by walls 1520. Sleeve 1500 can be constructed of metal, stainless steel, aluminum, plastic, polycarbonate, etc. Seals 4200, such as o-rings, can resist gas leakage, such as past pusher 4100 and/or out of housing 1100. Thus, pusher 4100 can function as a piston traveling within a cylinder, although it is not necessarily required that the cross-sectional shape of sleeve 1500 be round.

Medicament actuator 4000 can interface with medicament storage assembly 5000. For example, medicament actuator 4000 can comprise a plurality of plungers 4300, each of which can be capped with a piston 4400 which can sealingly slide and/or move within a corresponding vial 5100 containing a liquid medicament 5200. For example, in response to pressure applied by an actuating portion of the contents 2500 of compressed gas container 2400, pusher 4100 can cause plungers 4300 and/or pistons 4400 to simultaneously move. The number of corresponding sets of plungers 4300, pistons 4400, and/or vials 5100 can be 2, 3, 4, 5, 6, or more. Pistons 4400 can be constructed of a resilient, durable, and/or sealing material, such as a rubber. Each plunger 4300 from the plurality of plungers can define a longitudinal axis, the longitudinal axes (e.g., axes 4310, 4320, 4330, 4340) of the plurality of plungers parallel, non-coaxial, and/or co-planar.

Each vial 5100 from the plurality of vials can be substantially cylindrical with a substantially round and/or substantially elliptical cross-sectional shape. Thus, each vial 5100 can define a longitudinal axis, the longitudinal axes of the plurality of vials parallel, non-coaxial, and/or co-planar. The longitudinal axis of each vial can be co-axial with the longitudinal axis of its corresponding plunger.

Each vial can be capped at one end with a frangible 5300, which can be burst when piston 4400 generates sufficient pressure upon medicament 5200, thereby allowing at least a portion of medicament 5200 to flow out of vial 5100 and into medicament carrier 9000. Thus, the plurality of vials can be fluidly coupleable to the actuating portion of the contents 2500 of gas container 2400.

Medicament carrier 9000 can hold each of vials 5100 and can travel within sleeve 1500. Medicament carrier 9000 can comprise a plurality of channels 9200 adapted to receive medicament 5200 as it exits its respective vial 5100, and direct medicament 5200 to a common conduit 9300. Medicament carrier 9000 can interface with needle assembly 6000 and/or use indicator 7000.

From common conduit 9300, medicament 5200 can enter needle assembly 6000, such as into a single needle 6100 via which medicament can approach needle tip 6200. As medicament actuator 4000 and/or medicament carrier 9000 are driven toward actuator bar 1300, needle tip 6200 can penetrate an end 6400 of needle sheath 6300 and exit actuator bar 1300 at needle port 1340.

Figure 5:
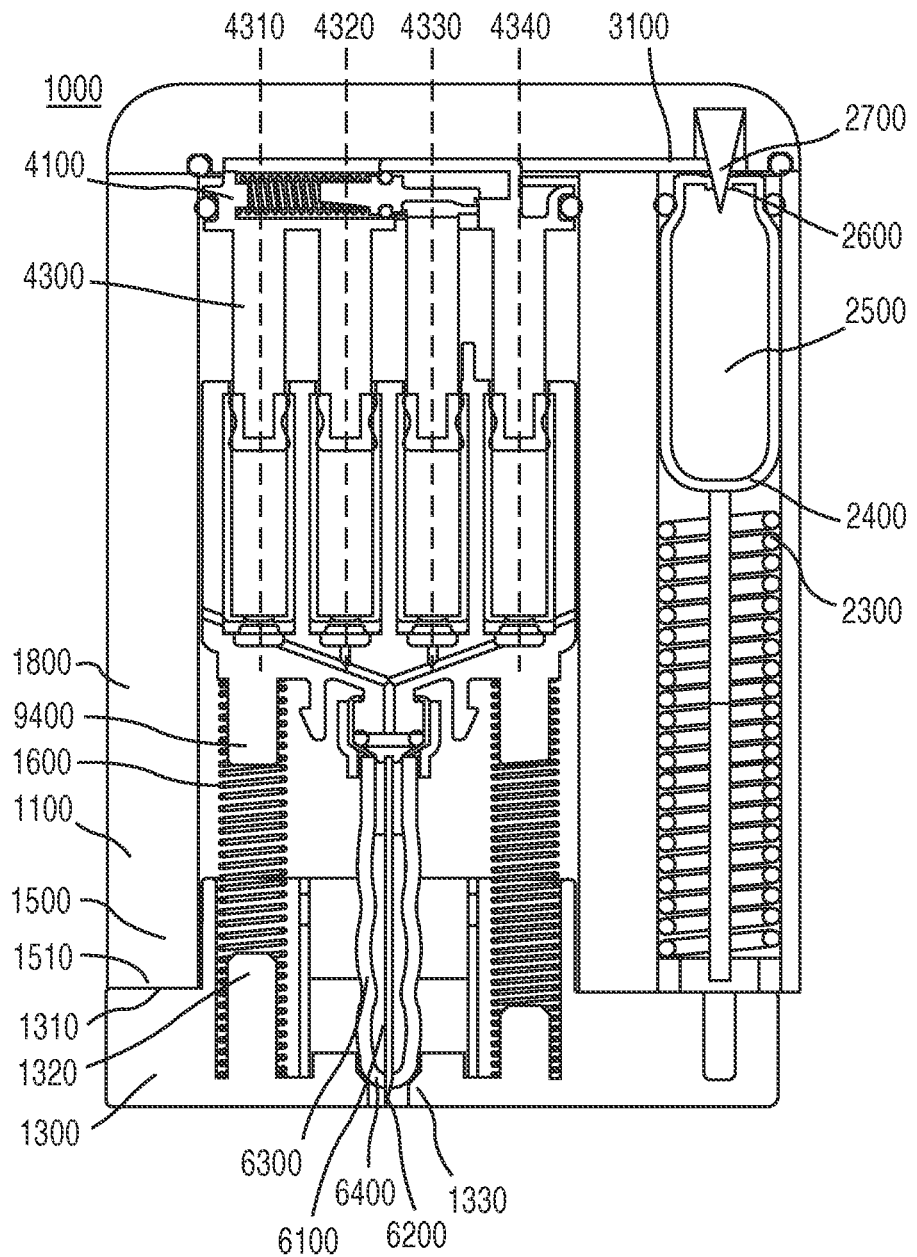
FIG. 5 is a cross-sectional view taken along lines A-A of FIG. 3 of an exemplary embodiment of a system 1000 in a second operative position.

Referring to FIG. 5, upon movement of actuation bar 1300 closer to handheld portion 1800, sheath seat 1330 can come in contact with sheath tip 6400, thereby causing sheath 6300 to buckle and/or crumble. As actuator bar 1300 comes in contact with handheld portion 1800, bar stop 1320 can approach medicament carrier stop 9400, while carrier spring 1600 is compressed.

Figure 6:
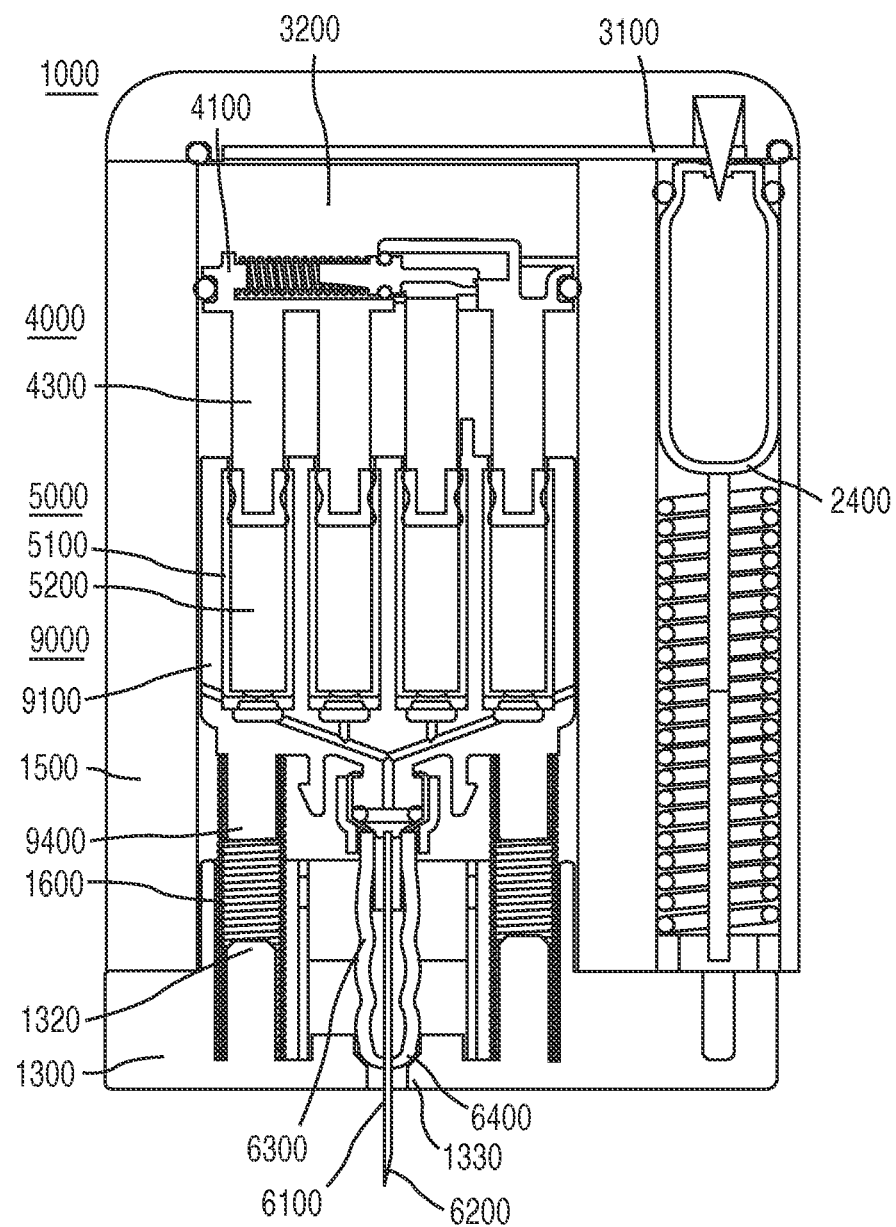
FIG. 6 is a cross-sectional view taken along lines A-A of FIG. 3 of an exemplary embodiment of a system 1000 in a third operative position.

Referring to FIG. 6, as at least a portion of contents 2500 of gas container 2400 escapes, it can flow through channel 3100. The gas, which can still be relatively pressurized, can begin to accumulate behind pusher 4100 to form an expanding gas chamber 3200 and to cause medicament actuator 4000, medicament storage assembly 5000, and medicament carrier 9000 to slide together within sleeve 1500. As medicament actuator 4000, medicament storage assembly 5000, and medicament carrier 9000 slide closer to actuator bar 1300, spring 1600 becomes increasingly compressed between bar stop 1320 and medicament carrier stop 9400. As medicament actuator 4000, medicament storage assembly 5000, and medicament carrier 9000 slide closer to actuator bar 1300, needle tip 6200 can extend further from actuator bar 1300 and sheath 6300 can become further compressed and/or deformed. At its ultimate extension point, needle tip 6200 can extend from housing 1100 from approximately 0.25 millimeters to approximately 20 millimeters, including all values and subranges therebetween, such as up to approximately 2 millimeters, greater than approximately 5 millimeters, from approximately 5.13 millimeters to approximately 9.98 millimeters, etc.

Figure 7:
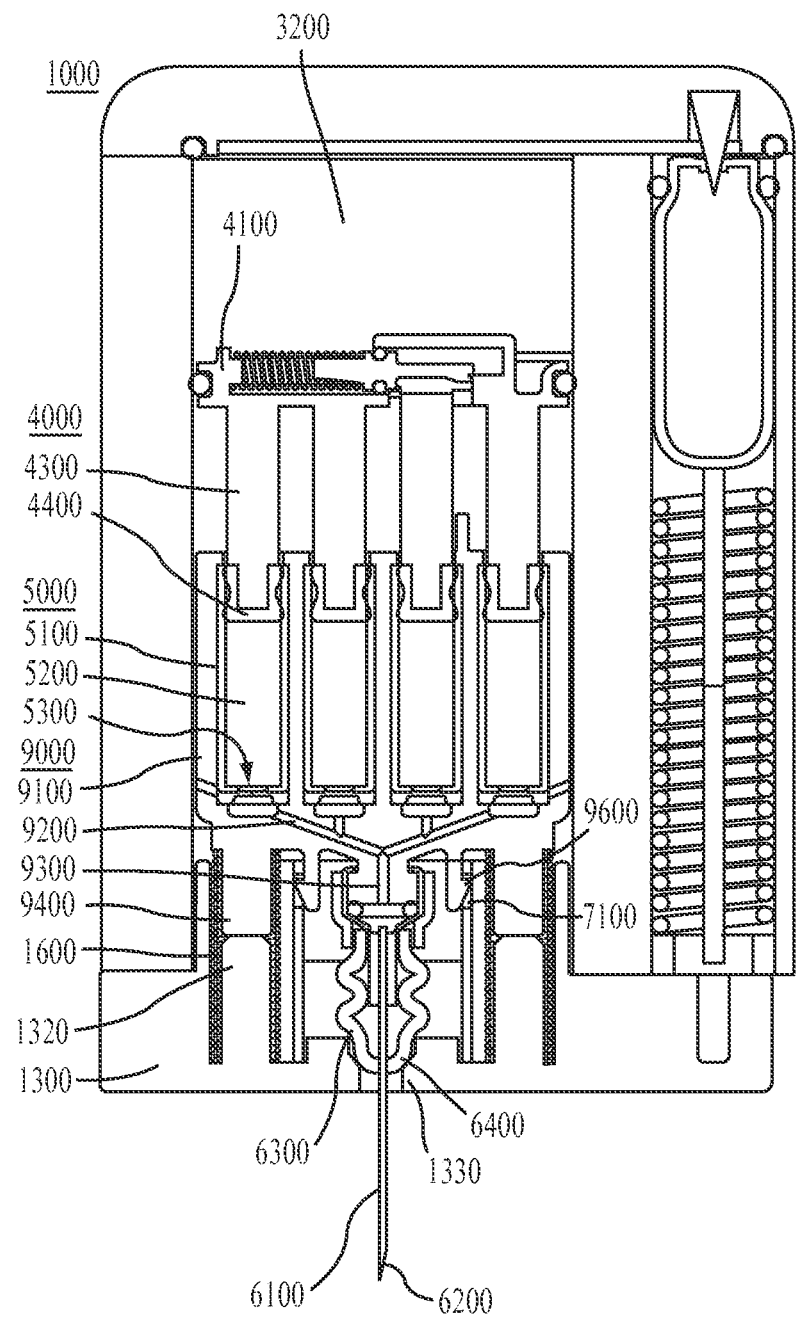
FIG. 7 is a cross-sectional view taken along lines A-A of FIG. 3 of an exemplary embodiment of a system 1000 in a fourth operative position.

Referring to FIG. 7, as gas chamber 3200 continues to expand, medicament carrier 9000 can be driven until medicament carrier stop 9400 contacts actuator bar stop 1300 thereby resisting further travel of medicament carrier 9000. At that point, additional expansion of gas chamber 3200 can cause medicament actuator 4000, pusher bar 4100, plungers 4300, and/or pistons 4400 to initiate travel with respect to medicament storage assembly 5000, thereby generating an expulsion pressure in vials 5100, and/or thereby rupturing frangibles 5300 and allowing medicament 5200 to enter medicament carrier 9000, and begin flowing through medicament channels 9200, medicament conduit 9300, needle 6100, and/or out needle tip 6200 and into a patient. Alternatively, frangibles 5300 can be replaced and/or augmented by a frangible located at or near where medicament conduit 9300 couples to needle 6100. Frangibles 5300 can be constructed of a thin, taught, resilient, durable, and/or sealing material potentially having a predetermined yield strength, such as a rubber, such as chromo butyl rubber, and/or of a relatively brittle material potentially having a predetermined yield strength, such as ceramic, certain plastics, such as polystyrene, etc.

As medicament carrier stop 9400 contacts actuator bar stop 1300, medicament carrier hooks 9600 can engage with engagement receivers 7100 in use indicator 7000.

Figure 8:
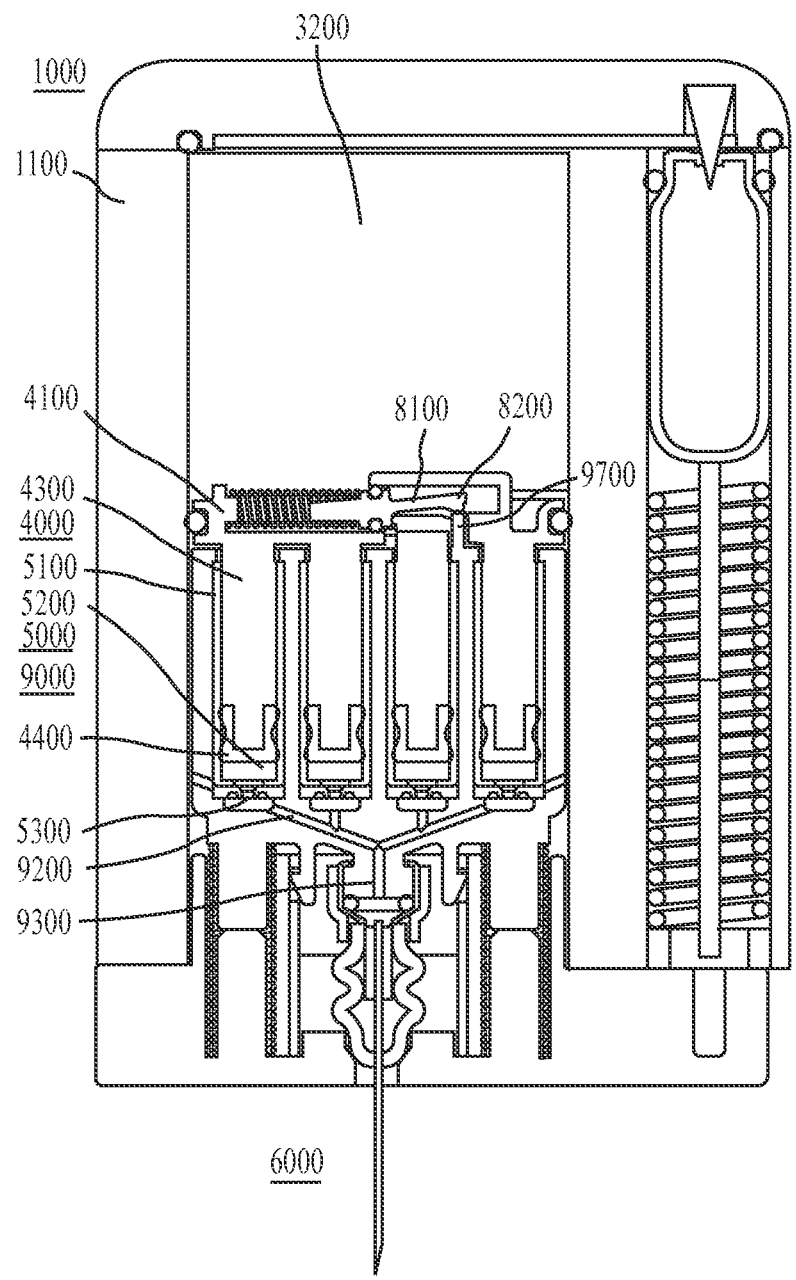
FIG. 8 is a cross-sectional view taken along lines A-A of FIG. 3 of an exemplary embodiment of a system 1000 in a fifth operative position.

Referring to FIG. 8, as gas chamber 3200 continues to expand, medicament actuator 4000, pusher bar 4100, plungers 4300, and/or pistons 4400 can continue moving until they complete their travel within medicament storage assembly 5000, thereby expelling a predetermined dose of medicament 5200 from vials 5100, out of needle assembly 6000, external to housing 1100, and/or into the patient. As gas chamber 3200 reaches its maximum size, medicament actuator 4000, pusher bar 4100, plungers 4300, and/or pistons 4400 can continue moving until they complete their travel with respect to medicament carrier 9000, thereby causing gas release actuator 9700 to engage with gas release valve 8200. Engagement of gas release actuator 9700 with gas release valve 8200 can cause within gas chamber 3200 to exit gas chamber 3200, discharge away from pistons 4400, and/or exhaust from system 1000 and/or housing 1100, such as via status indicator 1400 and/or a gas escape port located on housing 1100).

Figure 9:
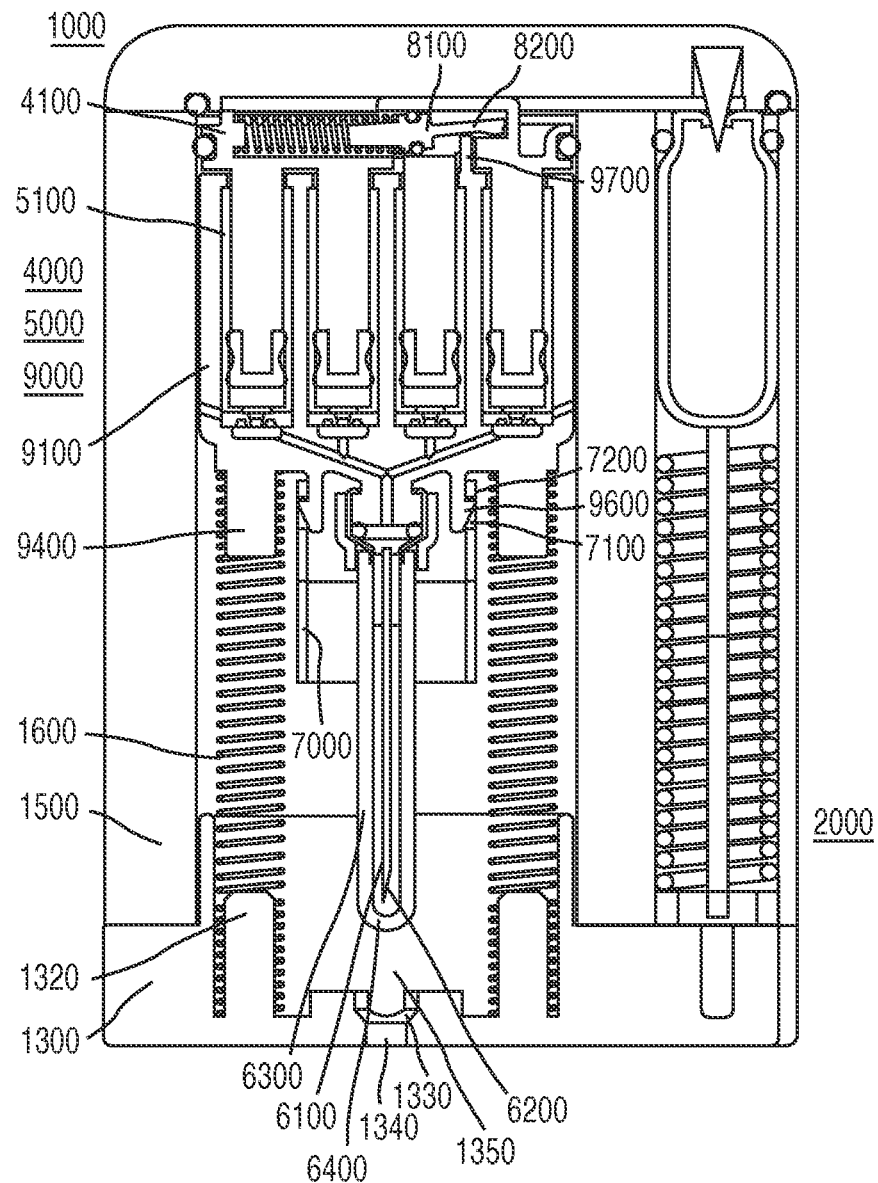
FIG. 9 is a cross-sectional view taken along lines A-A of FIG. 3 of an exemplary embodiment of a system 1000 in a sixth operative position.

Referring to FIG. 8 and FIG. 9, as sufficient gas is vented from gas chamber 3200, the pressure applied by the gas in gas chamber 3200 can decrease until the force applied by the gas on medicament actuator 4000 is less than the force of compressed spring 1600. Thus, spring(s) 1600 can begin to expand, thereby moving medicament carrier 9000, vial assembly 5000, and medicament actuator 4000 away from actuator bar 1300 and helping to exhaust gas from gas chamber 3200. As medicament carrier 9000 moves, use indicator 7000 can travel with it, due to the engaged relationship of medicament carrier hooks 9600 and engagement receivers 7100 and/or engagement catches 7200 in use indicator 7000. As use indicator 7000 moves away from actuator bar 1300, sheath 6300 can travel with it, thereby creating a gap between sheath tip 6400 and needle port 1340, and thereby exposing a previously non-visible colored portion 1350 of actuation bar 1300 and/or providing an indication that system 1000 has been used (and likely substantially exhausted of its medicament), thereby discouraging any further attempts to use system 1000.

As medicament carrier 9000 moves away from actuator bar 1300, needle 6100 can retract into sheath 6300 which un-buckles and/or un-deforms towards its original shape. Eventually, needle 6100 can retract completely within the boundaries of housing 1100, thereby tending to prevent accidental needle sticks after the initial injection and/or potentially reducing and/or eliminating a sharps hazard.

In certain exemplary embodiments, system actuator 2000 can comprise a finger triggered, twistable, pivotable, and/or lever-operated mechanism. For example, system actuator 2000 can comprise a twistable handle that can screw into gas port 2600. In certain exemplary embodiments, system actuator 2000 can be a finger trigger located on a side of the housing.

Figure 10:
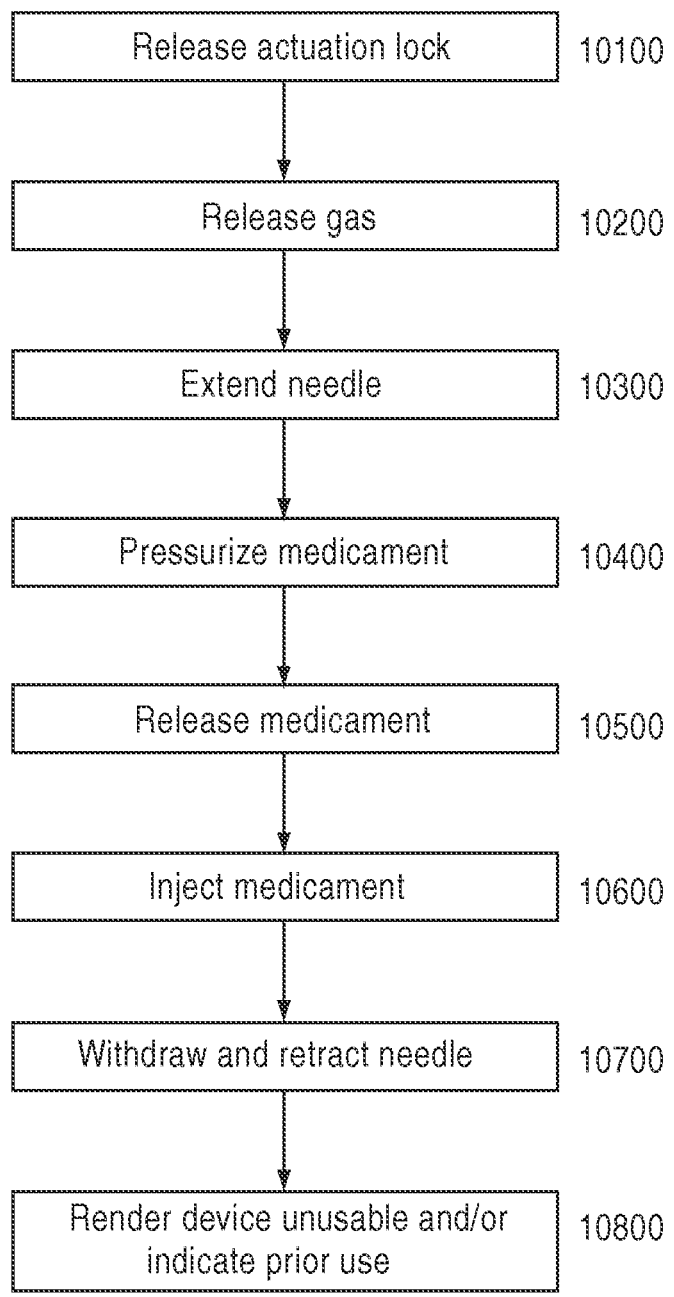
FIG. 10 is a flowchart of an exemplary embodiment of a method 10000.

FIG. 10 is a flowchart of an exemplary embodiment of a method 10000 for operating a medicament delivery apparatus. At activity 10100, an actuation lock for the apparatus is released. At activity 10200, an actuating portion of the contents of a compressed gas container are released. At activity 10300, via pressure provided by the released gas, a needle is extended from the apparatus. At activity 10400, via pressure provided by the released gas, a piston applies pressure to a medicament stored in one of a plurality of vials. At activity 10500, a frangible containing the medicament in the vial is burst. At activity 10600, the medicament flows from the vial, through the needle, and into a patient. At activity 10700, once a predetermined dose is expelled and/or injected, the needle is withdrawn from the patient and/or retracted into the pre-use bounds of the apparatus. At activity 10800, the apparatus is rendered unusable for additional injections and/or indicated as previously utilized.

Figure 11:
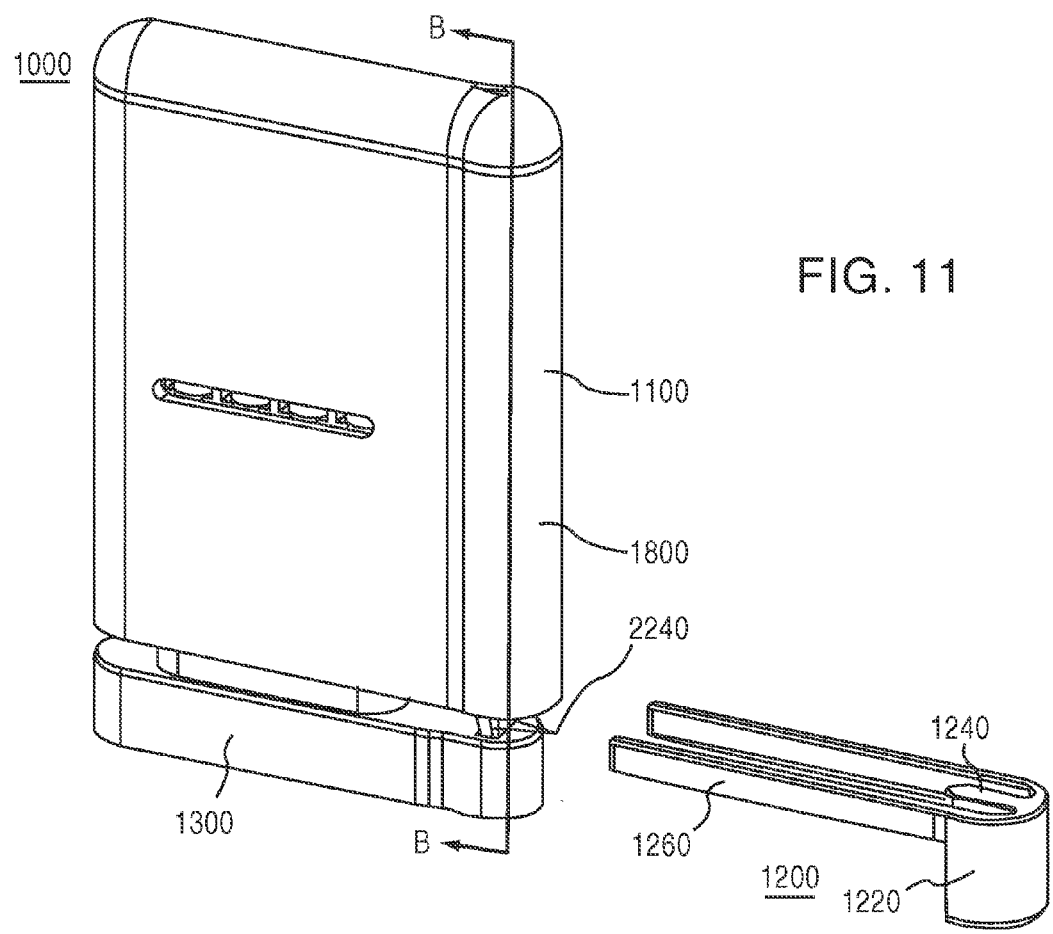
FIG. 11 is a perspective view of an exemplary embodiment of system 1000.

FIG. 11 is a perspective view of an exemplary embodiment of system 1000, showing actuation guard 1200 removed from housing 1100, so that actuation guard 1200 no longer separates actuator bar 1300 from handheld portion 1800. Actuation guard 1200 can comprise a grippable portion 1220 that can be gripped by a user to pull actuation guard 1200 away from housing 1100, thereby allowing system 1000 to be activated, such as via slapping actuator bar 1300 against a thigh of the user. Actuation guard 1200 can comprise an actuation stick separator portion 1240, that can keep separate actuation stick prongs 2240 when actuation guard 1200 is installed on housing 1100. Actuation guard 1200 can comprise a guard portion 1260 that can separate actuator bar 1300 from handheld portion 1800 when system 1000 is not in use and/or when system 1000 has not been used.

Figure 12:
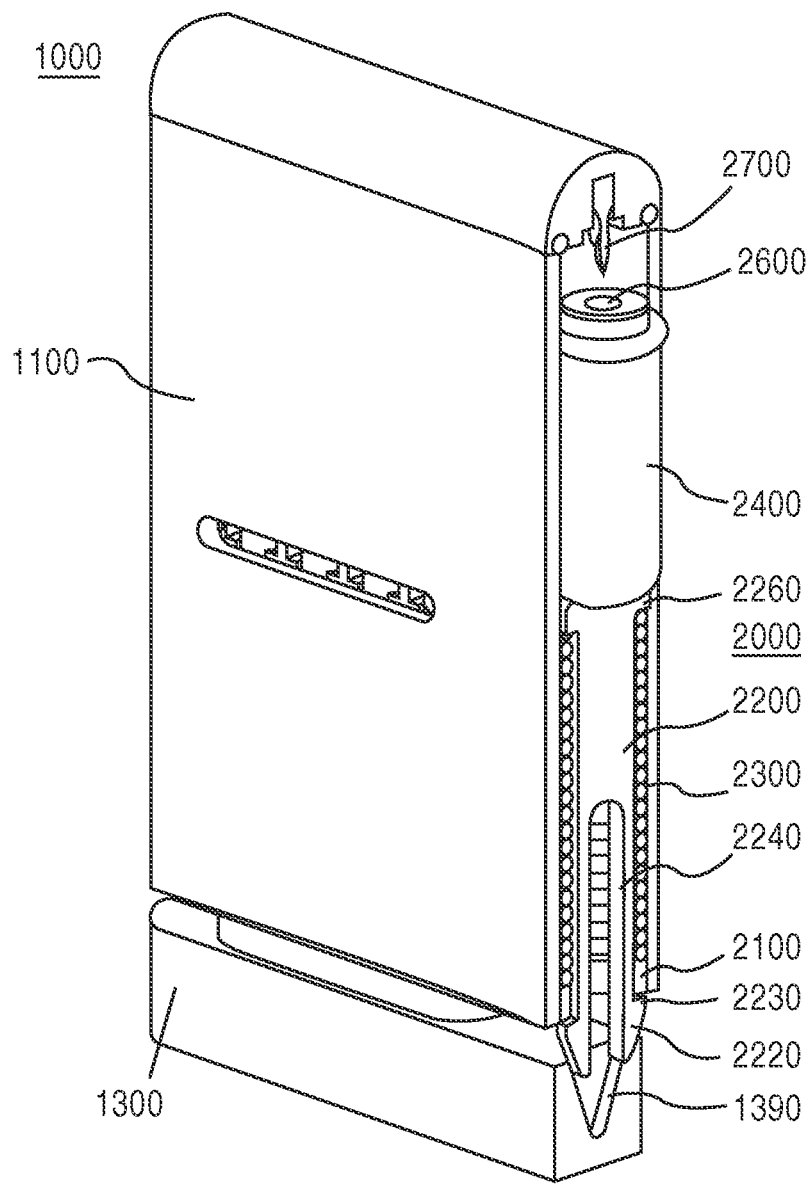
FIG. 12 is a perspective cross-sectional view taken along lines B-B of FIG. 11.
Figure 13:
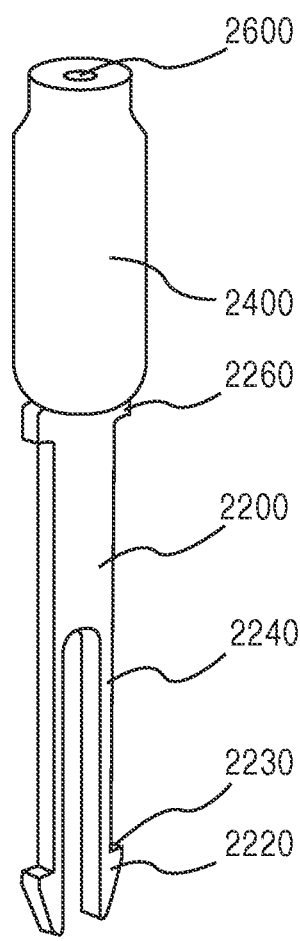
FIG. 13 is a perspective view of an exemplary embodiment of actuation stick 2200.

FIG. 12 is a perspective cross-sectional view taken along lines B-B of FIG. 11, and FIG. 13 is a perspective view of an exemplary embodiment of actuation stick 2200. Referring to FIGS. 12 and 13, system 1000 can comprise housing 1100, actuation bar 1300, and system actuator 2000, which can comprise prong squeezer 1390, actuation stick 2200, prong retainer 2100, spring 2300, upper spring retainer 2260, gas container 2400, gas port 2600, and/or puncturer 2700. When actuation bar 1300 is pressed firmly against a user's body, such as via slapping housing actuation bar against the user's thigh, buttocks, and/or arm, prong squeezer 1390 can urge prong tips 2220 of prongs 2240 of actuation stick 2200 toward one another. Note that prong tips 2200 can have a triangular, wedge, angular, and/or frustro-conical shape. As prongs tips 2220 slide along the angled V-groove of prong squeezer 1390, prong catches 2230 can substantially loose contact with prong retainer 2100. This can allow compressed spring 2300 to rapidly urge actuation stick 2200 and gas container 2400 toward puncturer 2700, which can penetrate gas port 2600, thereby allowing gas to escape from gas container 2400. Although any of many different types of gas containers can be utilized, an exemplary gas container can be obtained from Leland Limited, Inc. of South Plainfield, N.J.

Figure 14:
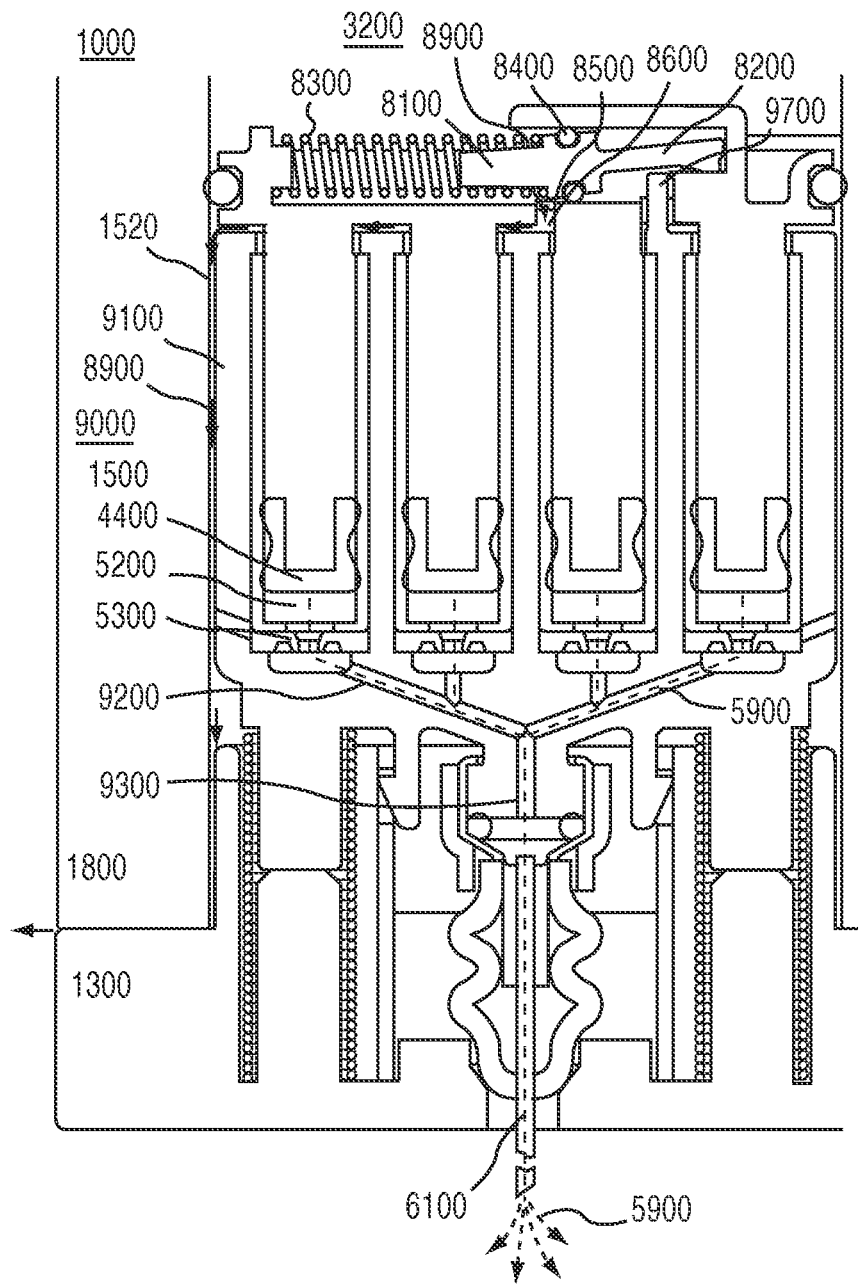
FIG. 14 is a cross-sectional view of an exemplary embodiment of gas venting mechanism 8000 taken along lines A-A of FIG. 3.

FIG. 14 is a cross-sectional view of an exemplary embodiment of gas venting mechanism 8000 of system 1000 taken along lines A-A of FIG. 3. System 1000 can comprise handheld portion 1800, actuator bar 1300, sleeve 1500. As pistons 4440 near the limit of their travels, medicament 5200 can be expelled along medicament path 5900, which can extend past frangible 5300, through medicament channels 9200, medicament conduit 9300, and needle 6100, and into the body of a user, such as subcutaneously, intramuscularly, and/or at a depth of from approximately 0.25 millimeters to approximately 20 millimeters, including all values and subranges therebetween, such as up to 2 millimeters, greater than 5 millimeters, etc.

As pistons 4440 near the limit of their travels, engagement of gas release actuator 9700 with gas release valve 8200 can cause compressed spring 8300 to move valve arm such that o-ring 8400 is urged away from its seat 8500. This movement can reveal a passage 8600, via which gas can exit gas chamber 3200 along gas exhaust path 8900, which can extend between sleeve inner walls 1520 and outer walls 9100 of medicament carrier 9000. Eventually, gas exhaust path 8900 can extend between handheld portion 1800 and actuator bar 1300. Likewise, an alternative embodiment of valve 8200, made of rubber or any other resilient material, can be placed across seat 8500 to provide a seal that, once gas release actuator 9700 interacts with valve 8200, allows valve 8200 to bend or flap upwards away from seat 8500, causing the gas to escape via passage 8600.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all subranges therein. Any information in any material (e.g., a United States patent, United States patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

What is claimed is:

1. An apparatus comprising:
   a housing;
   a medicament carrier moveably disposed within the housing;
   a delivery member;
   an energy storage member configured to produce a force via a pressurized gas to move the medicament carrier from a first carrier position to a second carrier position, the delivery member disposed within the housing when the medicament carrier is in the first carrier position, a portion of the delivery member extending from the housing when the medicament carrier is in the second carrier position;
   a moveable member configured to move between a first moveable member position and a second moveable member position when the carrier moves from the first carrier position to the second carrier position, the moveable member configured to move from the second moveable member position to a third moveable member position when the carrier is in the second carrier position, the moveable member configured to discharge a medicament through the delivery member when moving from the second moveable member position to the third moveable member position; and
   a release mechanism coupled to the moveable member, the release mechanism including a valve configured to engage a protrusion disposed on a proximal portion of the medicament carrier when the moveable member is in the third moveable member position, the valve configured to release the pressurized gas thereby releasing the force from the medicament carrier when the moveable member is in the third moveable member position to allow medicament carrier to move from the second carrier position towards the first carrier position.

2. The apparatus of claim 1, wherein the moveable member is substantially stationary relative to the medicament carrier when the medicament carrier moves from the first carrier position to the second carrier position.

3. The apparatus of claim 1, wherein the energy storage member is operably coupled to the moveable member such that the force is exerted on moveable member to cause the moveable member to move from the first moveable member position to the second moveable member position.

4. The apparatus of claim 1, further comprising:
   a medicament container coupled to the delivery member, the medicament container including a seal operable to fluidically isolate the medicament container from the delivery member, the seal configured to be ruptured when the moveable member moves from the second moveable member position towards the third moveable member position.

5. The apparatus of claim 1, further comprising:
   a medicament container coupled to the delivery member, the medicament container including epinephrine.

6. The apparatus of claim 1, wherein the delivery member is a needle.

7. The apparatus of claim 1, further comprising a biasing member configured to urge the medicament carrier towards the first carrier position.

8. The apparatus of claim 1, further comprising a retraction spring configured to urge the medicament carrier towards the first carrier position, a longitudinal axis of the retraction spring being offset from a longitudinal axis of the delivery member.

9. An apparatus comprising:
   a housing;
   a medicament container disposed within the housing, the medicament container operably coupled to a delivery member;
   an energy storage member configured to produce a force;
   a carrier moveably disposed within the housing and coupled to the medicament container such that the delivery member is disposed within the housing when the carrier is in a first position and at least a portion of the delivery member is outside of the housing when the carrier is in a second position;
   a piston configured to transfer at least a portion of the force to the carrier and a medicament within the medicament container to move the carrier from the first position to the second position and to deliver the medicament from the medicament container via the delivery member when the carrier is in the second position; and
   a release mechanism configured to release the force from the piston when the release mechanism is actuated, the carrier including a protrusion configured to actuate the release mechanism after the portion of the medicament has been delivered.

10. The apparatus of claim 9, further comprising:
    a biasing member configured to urge the carrier from the second position towards the first position.

11. The apparatus of claim 9, wherein the force is a first force, the apparatus further comprising:
    a retraction member configured to produce a second force to move the carrier from the second position towards the first position when the release mechanism has been actuated.

12. The apparatus of claim 9, further comprising:
    the medicament container includes a seal operable to fluidically isolate the medicament container from the delivery member, the seal configured to be ruptured when the portion of the force is transferred to the medicament within the medicament container via the piston.

13. The apparatus of claim 9, wherein the medicament includes epinephrine.

14. The apparatus of claim 9, wherein:
    the energy storage member is configured to produce a pressurized gas; and the release mechanism includes a valve configured to release the pressurized gas, the valve coupled to a proximal end portion of the piston, the protrusion of the carrier configured to engage the valve after the portion of the medicament has been delivered.

15. A method, comprising:

moving, within a housing, a carrier coupled to a medicament container from a first carrier position to a second carrier position, a needle disposed within the housing when the carrier is in the first carrier position, a portion of the needle disposed outside of the housing when the carrier is in the second carrier position;

moving, in response to a force produced by an energy storage member via a pressurized gas, a moveable member from a first moveable member position to a second moveable member position when the carrier is in the second carrier position to expel at least a portion of a medicament from the medicament container via the needle; and contacting a protrusion of the carrier with a portion of a release mechanism to open a valve of the release mechanism to release the pressurized gas when the moveable member is in the second moveable member position after the portion of the medicament has been expelled, the release mechanism configured to release the force from the moveable member when the release member is actuated.

16. The method of claim 15, wherein the force is a first force, the method further comprising:

moving, after the contacting and in response to a second force produced by a biasing member, the carrier from the second carrier position towards the first carrier position such that the needle is retracted into the housing.

17. The method of claim 15, wherein the release mechanism is coupled to the moveable member.

* * * * *